United States Patent [19]

Li

[11] Patent Number: 5,250,054
[45] Date of Patent: Oct. 5, 1993

[54] INTRACORPOREAL KNOT TYING APPARATUS AND METHOD

[75] Inventor: Lehmann K. Li, Wellesley, Mass.

[73] Assignee: Li Medical Technologies, Inc., Milford, Conn.

[21] Appl. No.: 877,462

[22] Filed: May 1, 1992

[51] Int. Cl.⁵ .............................................. A61B 17/00
[52] U.S. Cl. ....................................... 606/148; 606/1; 606/139; 606/144
[58] Field of Search ................... 606/1, 106, 108, 110, 606/126, 139, 144, 147, 148; 128/4, 897; 604/15, 16, 17, 18, 158, 164, 166, 264, 280, 281, 282

[56] References Cited

U.S. PATENT DOCUMENTS

| | | | |
|---|---|---|---|
| 3,877,434 | 4/1975 | Ferguson et al. | 606/139 |
| 4,157,709 | 6/1979 | Schuster et al. | 604/158 |
| 4,177,813 | 12/1979 | Miller et al. | 606/139 |
| 4,509,518 | 4/1985 | McGarry et al. | 606/143 |
| 4,562,839 | 1/1986 | Blake, III et al. | 606/143 |
| 4,796,626 | 1/1989 | DeVries | 606/148 |
| 4,846,799 | 7/1989 | Tanaka et al. | 604/158 |
| 4,854,330 | 8/1989 | Evans, III et al. | 604/264 |
| 4,887,996 | 12/1989 | Bengmark | 604/281 |
| 5,054,501 | 10/1991 | Chuttani et al. | 604/282 |

FOREIGN PATENT DOCUMENTS

| 3335696 | 4/1985 | Fed. Rep. of Germany | 606/16 |
|---|---|---|---|
| 1309971 | 5/1987 | U.S.S.R. | 606/144 |

*Primary Examiner*—Stephen C. Pellegrino
*Assistant Examiner*—Jeffrey A. Schmidt
*Attorney, Agent, or Firm*—Pandiscio & Pandiscio

[57] ABSTRACT

Apparatus and method for tying knots in suture at a interior surgical site. The apparatus comprises an elongated hollow member having a distal portion extending at an acute angle to the major longitudinal axis of the hollow member and terminating in a distal end surface, and a rod being partly flexible along its length and having a J-shaped hook at its distal end, wherein the hook is sized to grapple the suture which is to be manipulated by said device. The rod is received within the interior of the hollow member and adapted to reciprocate relative to the hollow member so that the hook can be moved between (i) an extended position wherein the mouth of the hook is spaced from the distal end surface of the hollow member by more than the thickness of the suture, whereby the suture can be grappled by the hook, (ii) an intermediate position wherein the mouth of the hook is spaced from the distal end surface of the hollow member by less than the thickness of the suture, but the interior base of the hook is spaced from the distal end surface of the hollow member by more than the thickness of the suture, whereby a suture grappled by the hook will be slidably captured to the hollow member, and (iii) a withdrawn position wherein the interior base of the hook is spaced from the distal end surface of the hollow member by less than the thickness of the suture, whereby a suture grappled by the hook will be fixedly captured to the hollow member.

16 Claims, 4 Drawing Sheets

Fig. 9

INTRACORPOREAL KNOT TYING APPARATUS AND METHOD

FIELD OF THE INVENTION

This invention relates to laparoscopic surgery in general, and more particularly to apparatus and methods for tying knots inside the body during such surgery.

BACKGROUND OF THE INVENTION

In laparoscopic surgery, access is gained to an interior surgical site by making one or more short incisions in the body which extend down to the interior surgical site, and then inserting a hollow tube or cannula into each incision so that the cannulas can act as liners to hold the incisions open and thereby provide portals leading down to the interior surgical site. A laparoscopic procedure can then be performed by passing instruments (e.g. cutting devices, clamps, viewing apparatus, etc.) down the cannulas so that the distal working ends of the instruments can be positioned and used about the surgical site, while the proximal handle ends of the instruments remain outside the body where they can be grasped by the surgeon.

Laparoscopic procedures frequently involve the repair and/or removal of tissue from the interior surgical site, and often require that some sort of closure be made to the tissue which is being operated upon. Such closure can be effected through the use of conventional needles and suture, surgical clips or staples, or other known closure means. In this respect, it has been found that the use of conventional needles and suture can have significant advantages in many laparoscopic procedures, since they generally allow the tension of the closure to be dynamically adjusted during suture deployment. At the same time, however, the use of conventional needles and suture can also present significant difficulties in laparoscopic surgery, on account of the limited access provided to, and at, the interior surgical site.

One aspect of using conventional needles and suture which can be particularly difficult to accomplish in a laparoscopic setting is that of tying knots. In particular, it has been found that it can be very difficult to properly manipulate the suture ends within the body so as to tie the knots, given the limited space available adjacent the interior surgical site. In addition, it will also be appreciated that the remote nature of the surgical site, and the limited cannula access provided to that site, further complicates this procedure.

Currently, surgeons generally use long straight forceps to reach into the interior surgical site to manipulate the suture ends during knot tying. This tends to be a time-consuming and inconvenient method to tie knots in a laparoscopic setting. In addition, such long forceps tend to offer limited suture control at the surgical site, since there is essentially no tactile feedback to the user when grasping the suture and no reliable way to vary the degree of engagement between the forceps and the suture. Furthermore, with such forceps the outer diameter of the forceps changes according to the positioning of the forceps' jaw members; when the two jaws are opened wide, the forceps will have a relatively large outer diameter, and when the jaws are closed down, the forceps will have a relatively small outer diameter. This characteristic can present problems in certain surgical sites which may be too cramped to permit the forceps' jaws to open fully. In addition, the fact that the outer diameter of the forceps changes according to the positioning of the forceps' jaws means that the surgeon must take care to ensure that nothing is placed adjacent the jaws which might interfere with operation of the forceps' jaws. Thus, for example, suture cannot be coiled tightly about the exterior of the forceps' jaws when the jaws are closed and must thereafter be opened, since the wound suture might inhibit opening of the jaws.

OBJECTS OF THE INVENTION

Accordingly, one object of the present invention is to provide a novel device to facilitate knot-tying inside the body during a laparoscopic surgical procedure.

Another object of the present invention is to provide a novel method for tying knots inside the body during laparoscopic surgery.

And another object of the present invention is to provide a novel device for gripping and manipulating suture at a remote location within the body, wherein the device is capable of alternatively engaging the suture so as to hold it fast to the device or engaging the suture so that it can slip in a controlled manner relative to the device.

Still another object of the present invention is to provide a novel device for gripping and manipulating suture at a remote location within the body, wherein the device will maintain a substantially constant outer diameter at the working end of the device.

Yet another object of the present invention is to provide a novel device for gripping and manipulating suture at a remote location within the body, wherein the device can have suture coiled about its exterior surface at the working end of the device without interfering with the device's suture gripping and manipulating features.

SUMMARY OF THE INVENTION

These and other objects are achieved through the present invention, which comprises the provision and use of a suture manipulating device comprising an outer sheath and an inner rod.

In the preferred embodiment, the outer sheath comprises a straight, rigid distal portion, a flexible intermediate portion, and a straight, rigid proximal portion. The sheath's flexible intermediate portion is formed so that the longitudinal axis of the sheath's distal portion is normally aligned with the longitudinal axis of the sheath's proximal portion; at the same time, however, the sheath's flexible intermediate portion is capable of being elastically deformed so that the longitudinal axis of the sheath's distal portion can be moved out of alignment with the longitudinal axis of the sheath's proximal portion.

In the preferred embodiment, the inner rod comprises a straight, rigid distal portion, a bending intermediate portion and a straight, rigid proximal portion. The rod's bending intermediate portion is formed so that the longitudinal axis of the rod's distal portion normally resides at an acute angle (e.g. approximately 30 degrees) relative to the longitudinal axis of the rod's proximal portion, but is capable of being elastically deformed so that the longitudinal axis of the rod's distal portion can be brought into alignment with the longitudinal axis of the rod's proximal portion. The distal portion of the inner rod comprises a crochet-type hook disposed adjacent the distal tip of the inner rod.

In the preferred embodiment, the outer sheath and the inner rod are formed so that the length of the distal portion of the outer sheath is approximately the same as the length of the distal portion of the inner rod, and the length of the flexible intermediate portion of the outer sheath is approximately the same as the length of the bending intermediate portion of the inner rod. Preferably the length of the proximal portion of the outer sheath is somewhat less than the length of the distal portion of the inner rod so as to facilitate connecting the outer sheath and the inner rod to a preferred form of handle. The outer sheath and the inner rod are also formed so that the inner rod can make a close sliding fit within the interior of the outer sheath.

On account of the foregoing construction, when the inner rod is positioned within the outer sheath, the outer sheath and the inner rod can be moved relative to one another so as to assume:

(1) a first position wherein the distal tip of the inner rod is withdrawn slightly relative to the distal tip of the outer sheath, and the inner rod's bending intermediate portion is positioned within and constrained by the outer sheath's straight proximal portion, whereby the inner rod and the outer sheath will both be substantially straight and in longitudinal alignment with one another;

(2) a second position wherein the distal portion of the inner rod and the bending intermediate portion of the inner rod both project out of the distal portion of the outer sheath, and so that the longitudinal axis of the inner rod's distal portion is disposed at an acute angle to both the longitudinal axis of the inner rod's proximal portion and the longitudinal axis of the outer sheath; and (3) a third position wherein the distal tip of the inner rod is nearly aligned with the distal tip of the outer sheath and so that the bending intermediate portion of the inner rod is generally aligned with the flexible intermediate portion of the outer sheath, so that the longitudinal axis of the inner rod's distal portion will be aligned with the longitudinal axis of the outer sheath's distal portion, the longitudinal axis of the inner rod's proximal portion will be aligned with the longitudinal axis of the outer sheath's proximal portion, and the longitudinal axis of the inner rod's distal portion will be disposed at an acute angle to the longitudinal axis of the inner rod's proximal portion.

Two identical suture manipulating devices such as the one described above can be used as follows to tie two suture ends into a knot at a remote surgical site.

First, the two suture manipulating devices are picked up by the surgeon so that one device is held in the right hand and one device is held in the left hand. At the same time, the devices are arranged so that they are positioned in their aforementioned first positions, so that the outer sheath and inner rod are both substantially straight and in longitudinal alignment with one another. Then the devices are passed through cannulas down to the surgical site so that the distal end of each device is positioned adjacent the suture ends which are to be tied in a knot.

Next, the left hand device is moved toward its aforementioned second position so that its crochet-type hook is exposed out the distal end of the outer sheath. It will be appreciated that as this occurs the left hand device will move briefly through its aforementioned third position until its hook is exposed the desired amount. Then a first suture end is picked up in the crochet-type hook and the left hand device is positioned in its third position so that the suture is captured between the crochet-type hook of the inner rod and the distal tip of the outer sheath. It will be appreciated that the suture end can be slidably captured by the device if the crochet-type hook is positioned slightly outboard of the outer sheath's distal tip, or the suture end can be fixedly captured by the device if the crochet-type hook is pulled tight against the outer sheath's distal tip. Generally the device will be used to first slidably capture the suture end to the tool, whereby the precise positioning of the tool relative to the suture end can be safely adjusted, and then the crochet-type hook will be moved further inboard to fixedly capture the suture end to the tool.

Next, the right hand device is positioned in its aforementioned third position so that the distal ends of the outer sheath and inner rod are set at an acute angle to the proximal ends of the outer sheath and inner rod. Then the length of first suture end extending between the host tissue and the left hand device is wound around the distal end of the right hand device several times so as to form at least one suture coil about the distal end of the right hand device. Preferably this is accomplished by rotating the right hand device axially about its principal axis while its distal end is disposed adjacent the suture so that its distal tip whips around the extended suture so as to form several suture coils about the distal end of the right hand device; alternatively, this may be accomplished by holding the right hand device relatively steady and winding the extended suture around the distal end of the right hand device using the left hand device.

In this respect it is also to be appreciated that the precise number of suture coils formed about the distal end of the right hand device is determined by the type of knot which is to be formed at the surgical site. For example, one complete coil is used to form a standard suture throw; two complete coils are used to form a so-called "surgeon's throw", which is also known as a locking throw.

Once the suture coils have been formed about the distal end of the right hand device, the right hand device is moved toward its aforementioned second position so that its crochet-type hook is exposed out the distal end of the outer sheath, the second suture end is picked up in the crochet-type hook and the right hand device is positioned in its third position so that the suture is captured between the crochet-type hook of the inner rod and the outer sheath. Again, it will be appreciated that the suture end can be slidably captured by the device if the crochet-type hook is positioned slightly outboard of the outer sheath's distal tip, or the suture end can be fixedly captured by the device if the crochet-type hook is pulled tight against the outer sheath's distal tip. As noted previously, the device will generally be used to first slidably capture the suture end to the tool, whereby the precise positioning of the tool relative to the suture end can be safely adjusted, and then the crochet-type hook will be moved further inboard to fixedly capture the suture end to the tool.

Finally, the right hand device is pulled away from the left hand device so as to draw the second suture end through the several coils of the first suture end, thereby forming a suture throw.

The foregoing procedure may then be repeated one or more times as required so as to form the desired suture knot. In this respect, it is also to be appreciated that by using successive throws formed by coiling the suture about the distal end of the right hand device in alternating directions of rotation, rather than in identical directions of rotation, a square knot can be formed by laying two or more such throws upon one another. Stated another way, if it is desired to form a square knot at the surgical site, a first throw would be formed by coiling the suture about the right hand device in a first (e.g. either clockwise or counterclockwise) direction, and the second throw would be formed by coiling the suture about the right hand device in a second (i.e., either a counterclockwise or clockwise) direction, respectively. A person skilled in the art will readily appreciate that still other types of knots can be formed using the present apparatus as well. In fact, it will be appreciated that the present apparatus can be used to duplicate, in an intracorporeal setting, all of the knots typically utilized in open surgical settings.

Other forms of the suture manipulating device are also contemplated. Thus, for example, in one alternative embodiment the device's outer sheath is formed with a permanent helical spiral and the inner rod is formed out of a material which is resilient at least along the portion of the rod which reciprocates within the helical spiral. Such a construction provides a tool which can be inserted through a surgical cannula so as to reach the interior site, yet still provides an outer sheath which has its distal portion set at an angle to the longitudinal axis of the sheath's proximal portion so that suture can be coiled about the exterior of the sheath's distal portion. Similarly, in another alternative embodiment, the device's outer sheath is formed with one or more permanent bends in a two-dimensional plane, and the inner rod is formed out of a material which is resilient at least along the portion of the rod which reciprocates within the single bend. Again, this construction provides a tool which can be inserted through a surgical cannula so as to reach the interior site, yet still provides an outer sheath which has its distal portion set at an angle to the longitudinal axis of the sheath's proximal portion so that suture can be coiled about the exterior of the sheath's distal portion.

BRIEF DESCRIPTION OF THE DRAWINGS

Still other objects and features of the present invention will be more fully disclosed or rendered obvious by the following detailed description of the present invention, which is to be considered together with the accompanying drawings wherein like numbers refer to like parts and further wherein.

DETAILED DESCRIPTION OF THE INVENTION

Figure 1:
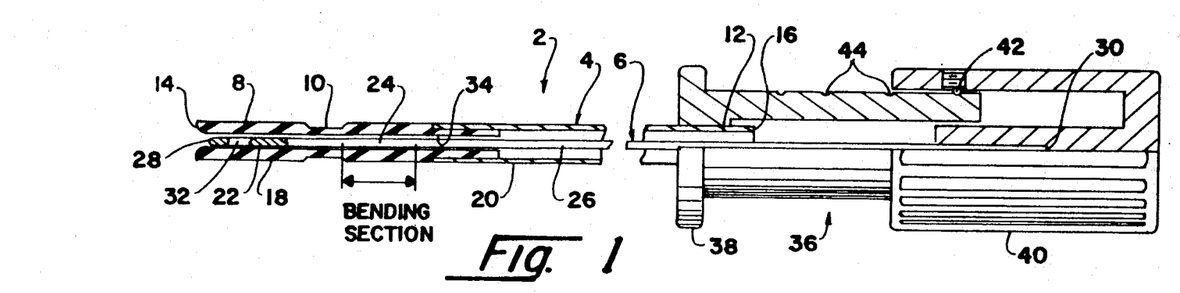
FIG. 1 is a side view in elevation, in partial section, showing a suture manipulating device formed in accordance with the present invention, wherein the device is shown in its aforementioned first position.
Figure 2:
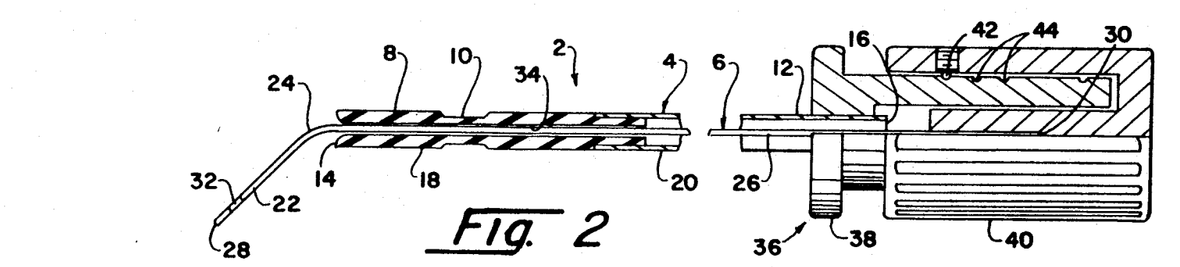
FIG. 2 is a side view in elevation, in partial section, showing the same suture manipulating device shown in FIG. 1, except that the device is shown in its aforementioned second position.
Figure 3:
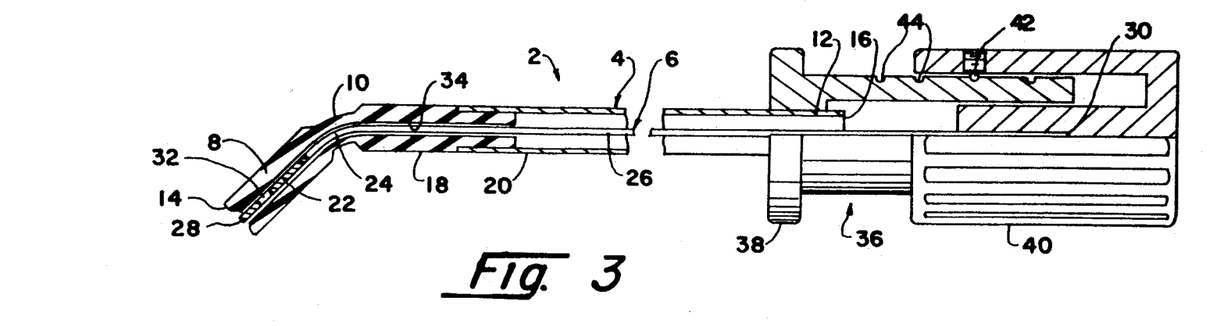
FIG. 3 is a side view in elevation, in partial section, showing the same suture manipulating device shown in FIG. 1, except that the device is shown in its aforementioned third position.

Looking first at FIGS. 1-3, there is shown a suture manipulating device 2 formed in accordance with the present invention. Suture manipulating device 2 comprises a preferred embodiment of the present invention, and generally comprises an outer sheath 4 and an inner rod 6.

Outer sheath 4 comprises a straight, rigid distal portion 8, a flexible intermediate portion 10, and a straight, rigid proximal portion 12. Outer sheath 4 terminates in a distal end 14 and a proximal end 16.

The sheath's flexible intermediate portion 10 is formed so that the longitudinal axis of the sheath's distal portion 8 is normally aligned with the longitudinal axis of the sheath's proximal portion 12 (FIGS. 1 and 2); at the same time, however, the sheath's flexible intermediate portion 10 is capable of being elastically deformed so that the longitudinal axis of the sheath's distal portion 8 can be moved out of alignment with the longitudinal axis of the sheath's proximal portion 12 (FIG. 3).

Outer sheath 4 can be formed in a variety of ways well known in the art. For example, sheath 4 can be formed by attaching a somewhat softer, somewhat elastic (e.g. rubber) cannula 18 to the front end of a relatively rigid (e.g. steel) cannula 20, wherein the softer somewhat elastic cannula 18 forms the sheath's distal portion 8, its flexible intermediate portion 10 and the front part of its proximal portion 12, and the relatively rigid cannula 20 forms the rear part of the sheath's proximal portion 12. In such a construction, softer cannula 18 has a sufficient hardness and thickness in the regions where it comprises the sheath's distal portion 8 and proximal portion 12 so as to be substantially rigid, yet has a reduced thickness in the region where it comprises the sheath's intermediate portion 10 so as to be substantially flexible. The precise material chosen to form cannula 18 can vary according to the application, but in general it is preferred that cannula 18 be formed out of a material which is as soft as, or softer, than the material which is used to form the suture, so as to ensure that cannula 18 will deform during suture engagement before the suture deforms, so as to protect the integrity of the suture. Alternatively, other equivalent structures may be used to form outer sheath 4.

Inner rod 6 comprises a straight, rigid distal portion 22, a bending intermediate portion 24, and a straight, rigid proximal portion 26. Inner rod 6 terminates in a distal end 28 and a proximal end 30.

The rod's bending intermediate portion 24 is formed so that the longitudinal axis of the rod's distal portion 22 normally resides at an acute angle (e.g. approximately 30 degrees) relative to the longitudinal axis of the rod's proximal portion 26 (FIGS. 2 and 3), but the bending intermediate portion 24 is capable of being elastically deformed so that the longitudinal axis of the rod's distal portion 22 can be brought into alignment with the longitudinal axis of the rod's proximal portion 26 (FIG. 1).

The distal portion 22 of inner rod 6 comprises a crochet-type hook 32 (see FIGS. 1-4, 4A, 5, 5A, 6 and 6A) which is disposed adjacent the distal end 28 of inner rod 6.

Inner rod 6 may be formed in a variety of ways well known in the art, e.g. inner rod 6 may be formed out of a single piece of steel rod which is bent as required so as to form the rod's bending intermediate portion 24, and worked as required so as to form the rod's crochet-type hook 32.

Outer sheath 4 and inner rod 6 are formed so that the length of the distal portion 8 of outer sheath 4 is approximately the same as the length of the distal portion 22 of inner rod 6, and the length of the flexible intermediate portion 10 of outer sheath 4 is approximately the same as the length of the bending intermediate portion 24 of inner rod 6. Preferably the length of the proximal portion 12 of outer sheath 4 is somewhat less than the length of the distal portion 26 of inner rod 6 so as to facilitate connecting outer sheath 4 and inner rod 6 to a handle of the sort described below.

Outer sheath 4 and inner rod 6 are also formed so that the inner rod can make a close sliding fit within the interior bore 34 of the outer sheath.

On account of the foregoing construction, when inner rod 6 is positioned within outer sheath 4, the outer sheath and the inner rod can be moved relative to one another so as to assume:

(1) a first position (FIG. 1) wherein the distal end 28 of inner rod 6 is withdrawn slightly relative to the distal end 14 of outer sheath 4, and the inner rod's bending intermediate portion 24 is positioned within and constrained by the outer sheath's straight proximal portion 12, whereby the inner rod and the outer sheath will both be substantially straight and in longitudinal alignment with one another;

(2) a second position (FIG. 2) wherein the distal portion 22 of inner rod 6 and the bending intermediate portion 24 of inner rod 6 both project out of the distal portion 8 of outer sheath 4, and so that the longitudinal axis of the inner rod's distal portion 22 is disposed at an acute angle (e.g. approximately 30 degrees) to the longitudinal axis of the inner rod's proximal portion 26, and at the same acute angle to the longitudinal axis of outer sheath 4; and (3) a third position (FIG. 3) wherein the distal tip 28 of inner rod 6 is nearly aligned with the distal tip 14 of outer sheath 4 and so that the bending intermediate portion 24 of the inner rod 6 is generally aligned with the flexible intermediate portion 10 of outer sheath 4, so that the longitudinal axis of the inner rod's distal portion 22 will be aligned with the longitudinal axis of the outer sheath's distal portion 8, and the longitudinal axis of the inner rod's proximal portion 26 will be aligned with the longitudinal axis of the outer sheath's proximal portion 12, and so that the longitudinal axis of the inner rod's distal portion 22 will be disposed at an acute angle (e.g. approximately 30 degrees) to the longitudinal axis of the inner rod's proximal portion 26.

A handle 36 is provided to telescope outer sheath 4 and inner rod 6 back and forth relative to one another so as to place the suture manipulating device 2 into its aforementioned first, second and third positions. In this respect, it will be appreciated that such telescoping of outer sheath 4 and inner rod 6 relative to one another may be achieved by holding outer sheath 4 fixed in place and moving inner rod 6 back and forth relative to the outer sheath, or by holding inner rod 6 fixed in place and moving outer sheath 4 back and forth relative to the inner rod, or by moving both outer sheath 4 and inner rod 6 back and forth relative to one another.

In the preferred embodiment shown in FIGS. 1-3, it is preferred that the telescoping of outer sheath 4 and inner rod 6 relative to one another be achieved by holding inner rod 6 fixed in place and moving outer sheath 4 back and forth relative to the inner rod. To this end, inner rod 6 is formed slightly longer than outer sheath 4, and handle 36 is formed with two telescoping portions, a distal portion 38 and a proximal portion 40. Distal portion 38 is securely attached to proximal portion 12 of outer sheath 4, and proximal portion 40 is securely attached to proximal portion 26 of inner rod 6. As a result of this construction, the surgeon can grasp the handle's proximal portion 40 with the palm of the hand and manipulate the handle's distal portion 38 toward and away from the handle's proximal portion 40 by using thumb and forefinger, whereby outer sheath 4 and inner rod 6 can be moved between the positions shown in FIGS. 1-3.

If preferred, a detent arrangement may be provided in handle 36 to help maintain outer sheath 4 and inner rod 6 in certain predetermined positions. By way of example, such a detent arrangement might comprise a spring-biased ball 42 mounted to proximal handle portion 40 and adapted to engage one of a plurality of surface openings 44 formed in distal handle portion 38. Alternatively, other equivalent detent arrangements may also be provided.

Figure 4:
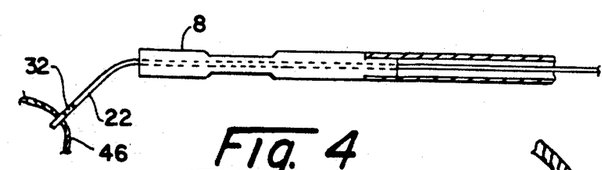
FIG. 4 is a view like that of FIG. 2, showing the distal tip of the suture manipulating device engaging a suture end.
Figure 4A:
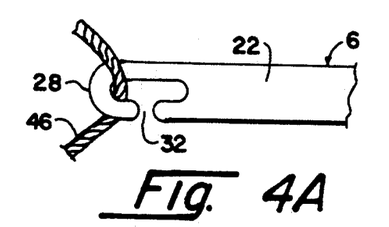
FIG. 4A is an enlarged view of selected portions of FIG. 4, showing the distal portion of the inner rod engaging the suture end, with the apparatus of FIG. 4A having been rotated approximately 90 degrees from the position shown in FIG. 4.

Looking next at FIGS. 4 and 4A, outer sheath 4 and inner rod 6 are formed so that the inner rod's crochet-type hook 32 can engage a suture end 46 in a sort of grappling hook manner when the inner rod's distal portion 22 is extended relative to the distal portion 8 of outer sheath 4. Furthermore, by thereafter moving outer sheath 4 distally relative to inner rod 6, in the manner shown in FIGS. 5 and 5A, the inner rod's crochet-type hook 32 can coordinate with the outer sheath's distal end 14 to slidingly capture suture end 46 to suture manipulating device 2. Finally, by thereafter moving outer sheath 4 even further distally relative to inner rod 6, in the manner shown in FIGS. 6 and 6A, the inner rod's crochet-type hook 32 can coordinate with the outer sheath's distal end 14 to lockingly capture suture end 46 to suture manipulating device 2. Preferably the outer sheath's distal portion 8 is bevelled slightly where its interior bore 34 meets its distal end 14 so as to minimize any possibility that the suture 46 might be damaged when it is lockingly captured to suture manipulating device 2 in this way. Furthermore, by forming at least the distal tip of outer sheath 4 out of a somewhat soft, somewhat elastic material, i.e., a material which is at least as soft as the material which is used to form the suture, the possibility of damaging suture 46 during locking engagement will be further reduced.

Figure 5:
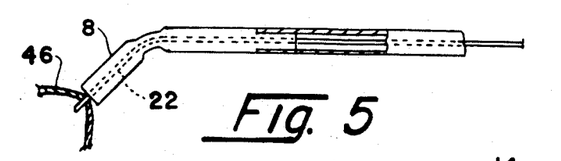
FIG. 5 is a view generally like that of FIG. 3, showing the distal tip of the suture manipulating device engaging a suture end and slidably capturing the suture end to the distal end of the outer sheath.
Figure 5A:
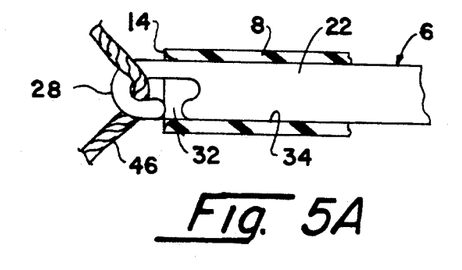
FIG. 5A is an enlarged view of selected portions of FIG. 5, showing the distal portion of the inner rod slidably capturing the suture end to the distal end of the outer sheath, with the apparatus of FIG. 5A having been rotated 90 degrees from the position shown in FIG. 5.
Figure 6:
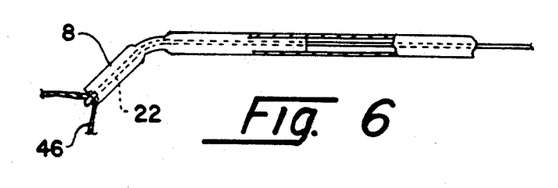
FIG. 6 is a view generally like that of FIG. 3, showing the distal tip of the suture manipulating device engaging a suture end and fixedly capturing the suture end to the distal end of the outer sheath.
Figure 6A:
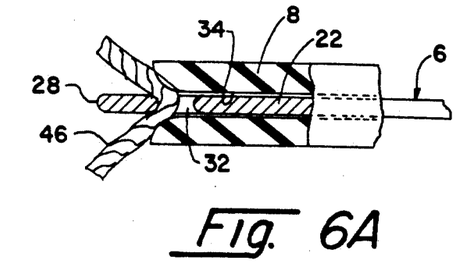
FIG. 6A is an enlarged view of selected portions of FIG. 6, showing the distal portion of the inner rod fixedly capturing the suture end to the distal end of the outer sheath.

Thus it will be seen that a suture manipulating device 2 can be used to pick up a loose suture end at the interior surgical site using its crochet-type hook, in the grappling hook manner shown in FIGS. 4 and 4A; to remain in engagement with that suture end while it is slid along the length of the suture to reach a desired point of attachment, in the manner shown in FIGS. 5 and 5A; and to securely grasp the suture end to the device at the desired point of attachment, in the manner shown in FIGS. 6 and 6A. Conventional long straight forceps are incapable of providing such suture control.

Two identical suture manipulating devices 2 may be used as follows to tie a knot in a pair of suture ends located within the body during a typical laparoscopic procedure.

Figure 7A:
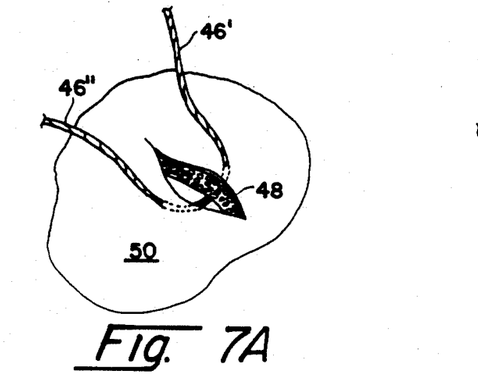
FIGS. 7A-7E show how two suture manipulating devices such as those shown in FIGS. 1-6 can be used to tie a knot at an interior surgical site.

More particularly, and looking next at FIG. 7A, there is shown a typical incision 48 formed in a piece of tissue 50 which is located at an interior surgical site. Access to incision 48 and tissue 50 is typically gained by means of one or more surgical cannulas (not shown) which extend from the region outside the body down to the interior surgical site. In a typical laparoscopic procedure, a suture 46 having a first suture end 46' and a second suture end 46" might be deployed across incision 48 and need to have its ends 46' and 46" tied in a knot so as to hold the incision closed. Two identical suture manipulating devices 2 may be used as is hereinafter described to tie a knot in first suture end 46' and second suture end 46".

First, the suture manipulating devices 2 are picked up by the surgeon so that one suture manipulating device 2R is held in the surgeon's right hand and one suture manipulating device 2L is held in the surgeon's left hand. At the same time, each of the suture manipulating devices 2 is arranged so that it is positioned in its aforementioned first position, in the manner shown in FIG. 1, so that the outer sheath 4 and inner rod 6 are substantially straight and in longitudinal alignment with one another. Then the two suture manipulating devices 2R and 2L are passed down the aforementioned cannulas to the surgical site so that the distal ends of suture manipulating devices 2R and 2L are positioned adjacent incision 48.

Next, the suture manipulating device 2L is positioned in (or at least moved toward) its aforementioned second position (see FIGS. 2, 4 and 4A) so that its crochet-type hook 32 is exposed out the distal end of outer sheath 4. It will be appreciated that as this occurs suture manipulating device 2L will move briefly through its aforementioned third position until its hook is exposed the desired amount. Then first suture end 46' is picked up in the crochet-type hook 32 with a grappling hook motion and the suture manipulating device 2L is positioned in its third position (FIG. 3) so that the suture is captured between the crochet-type hook 32 of inner rod 6 and the distal end 14 of outer sheath 4.

Figure 7B:
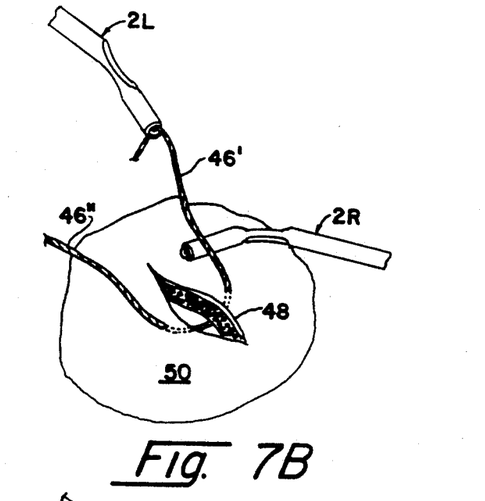

More particularly, it will be appreciated that the first suture end 46' can first be hooked by the suture manipulating device's hook 32 by putting the device in the position shown in FIGS. 4 and 4A (or in a position approaching that shown in FIGS. 4 and 4A); then first suture end 46' can be slidably captured to the suture manipulating device 2L by putting the device in the position shown in FIGS. 5 and 5A, whereupon the tool can be safely slid along the length of the suture until the desired point of attachment is reached; and finally the first suture end 46' can be fixedly captured by suture manipulating device 2L by putting the device in the position shown in FIGS. 6 and 6A. See generally FIG. 7B.

Figure 7C:
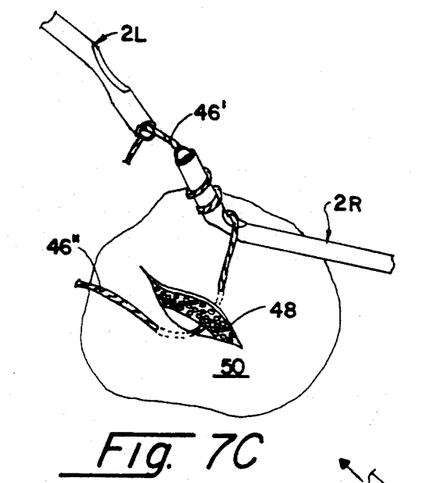

Next, the suture manipulating device 2R is positioned in its aforementioned third position (FIG. 3) so that the distal lengths of the outer sheath 4 and inner rod 6 are set at an acute angle (e.g. approximately 30 degrees) to the proximal lengths of the outer sheath 4 and inner rod 6. Then the length of first suture end 46' extending between the host tissue 50 and suture manipulating device 2L is wound around the distal portion 8 of suture manipulating device 2R several times so as to form at least one suture coil about the distal portion of suture manipulating device 2R. See generally FIG. 7C. It is to be appreciated that coiling first suture end 46' around the distal portion 8 of suture manipulating device 2R can be quickly and easily achieved simply by rotating suture manipulating device 2R about its principal axis, i.e., the longitudinal axis of the sheath's proximal portion 4, since the distal portion 8 will be set at an acute angle (e.g. approximately 30 degrees) to the axis of rotation (see FIGS. 3 and 7C). Alternatively, first suture end 46' may be coiled around the distal portion 8 of suture manipulating device 2R by holding suture manipulating device 2R relatively steady and winding first suture end 46' around the distal end of suture manipulating device 2R using suture manipulating device 2L.

In this respect it is also to be appreciated that the precise number of suture coils formed about the distal end of suture manipulating device 2R is determined by the type of knot which is to be formed at the surgical site. For example, one complete coil is used to form a standard suture throw; two complete coils are used to form a so-called "surgeon's throw", which is also sometimes referred to as a locking throw.

Figure 7D:
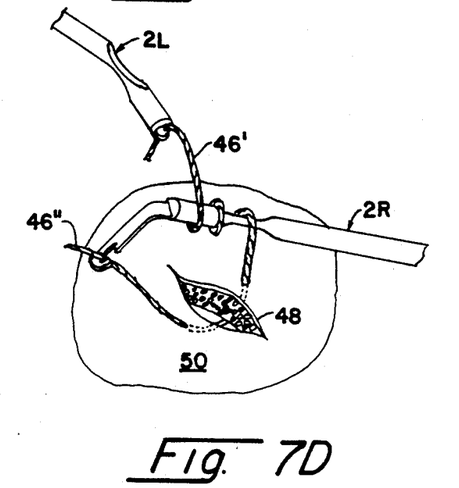

Once the suture coils have been formed about the distal end of suture manipulating device 2R, suture manipulating device 2R has its outer sheath 6 retracted so that the device approaches, but does not necessarily reach, its aforementioned second position (FIG. 2). In this way the tool's crochet-type hook 32 is exposed. Then the second suture end 46" is picked up in the exposed crochet-type hook 32. While this is being done, the length of first suture end 46' extending between the host tissue 50 and suture manipulating device 2L remains coiled about the distal portion of suture manipulating device 2R. See generally FIG. 7D.

Next, the suture manipulating device 2R is positioned in its third position (see FIG. 3) so that the second suture end 46" is captured between the crochet-type hook 32 of the inner rod 6 and the outer sheath 4.

More particularly, it will again be appreciated that the second suture end 46" can first be hooked by the suture manipulating device's hook 32 by positioning the device in the position shown in FIGS. 4 and 4A (or in a position approaching that shown in FIGS. 4 and 4A); then second suture end 46" can be slidably captured to the suture manipulating device 2R by putting the device in the position shown in FIGS. 5 and 5A, whereupon the tool can be safely slid along the length of the suture until the desired point of attachment is reached; and finally the second suture end 46" can be fixedly captured by the suture manipulating device 2R by putting the device in the position shown in FIGS. 6 and 6A. Again, all of this is done while the length of first suture end 46' between the host tissue 50 and suture manipulating 2L remains coiled about the distal portion of suture manipulating device 2R.

Figure 7E:
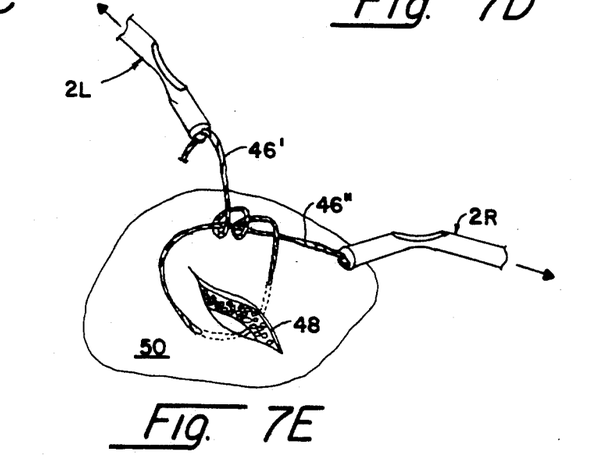

Next, suture manipulating device 2R is pulled away from suture manipulating device 2L so as to draw the second suture end 46" through the several coils of the first suture end 46' which formerly sat wrapped about the distal portion of suture manipulating device 2R, and so as to thereby form a suture throw. See generally FIG. 7E.

The foregoing procedure may then be repeated one or more additional times as required so as to form the desired suture knot at the surgical site. In this respect, it is also to be appreciated that by using successive throws formed by coiling the suture about the distal end of suture manipulating device 2R in alternating directions of rotation, rather than in identical directions of rotation, a square knot can be formed by laying two or more such throws upon one another. Stated another way, if it is desired to form a square knot at the surgical site, a first throw would be formed by coiling the suture about suture manipulating device 2R in a first (e.g. either clockwise or counterclockwise) direction, and the second suture throw would be formed by coiling the suture about suture manipulating device 2R in a second (i.e., either counterclockwise or clockwise) direction, respectively. It will be appreciated that still other types of knots can be formed using the present apparatus as well. In fact, the present apparatus can be used to duplicate, in an intracorporeal setting, all of the knots typically utilized in open surgical settings.

It is to be appreciated that suture manipulating device 2 maintains a substantially constant outer diameter at substantially all times, regardless of whether it is grappling a piece of suture in the manner shown in FIGS. 4 and 4A, slidably capturing the suture in the manner shown in FIGS. 5 and 5A, or fixedly capturing the suture in the manner shown in FIGS. 6 and 6A. This feature is a major improvement over the prior art forceps devices, which increase or decrease their outer diameters according to the positioning of their jaws. For one thing it means that suture manipulating device 2 can be used more conveniently in tight surgical locations; for another thing it means that lengths of suture (see, for example, FIGS. 7C-7E) can be conveniently wound around the distal end of the tool and then conveniently disengaged from the same, all without fear of inhibiting the suture grasping and manipulating characteristics of the tool, as occurs in the case of forceps tools. Thus it will be seen that suture manipulating tool 2 constitutes a significant improvement over the forceps tools of the prior art.

Furthermore, inasmuch as suture manipulating device 2 is adapted so that its distal portion 8 can be positioned at an acute angle (e.g. approximately 30 degrees) to the major longitudinal axis of the tool (i.e., the longitudinal axis of the sheath's proximal portion 16), coiling a length of suture about the distal portion of the tool can be quickly and easily accomplished simply by positioning the distal portion of the tool adjacent the suture to be coiled and then rotating the tool about the longitudinal axis of its proximal portion.

Numerous modifications may, of course, be made to the apparatus and method disclosed above without departing from the scope of the present invention. Thus, for example, an alternative handle arrangement of the sort well known in the art could be provided for moving outer sheath 4 and inner rod 6 back and forth relative to one another.

Furthermore, it is anticipated that only one suture manipulating device 2 could be used to form the desired intracorporeal knot. In such a situation, the single suture manipulating device would function as the device 2R identified above, and the device 2L could be replaced by conventional forceps or other equivalent means to hold suture end 46' extended away from host tissue 50.

It is also anticipated that other forms of suture manipulating devices may be provided without departing from the scope of the present invention.

Figure 8:
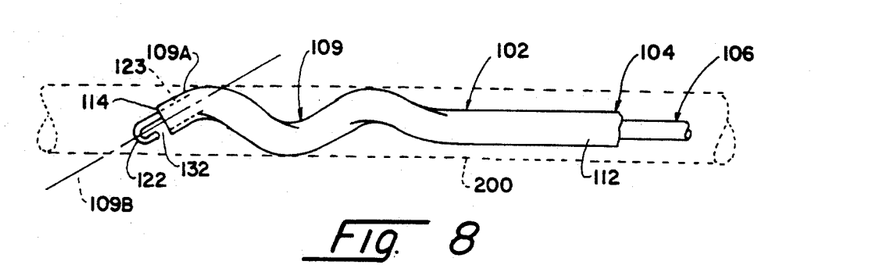
FIG. 8 is a side view in elevation showing the distal end of an alternative suture manipulating device also formed in accordance with the present invention.

Thus, for example, the distal end of such an alternative suture manipulating device 102 is shown in FIG. 8. Suture manipulating device 102 is identical to the suture manipulating device 2 previously described, except as will hereinafter be discussed in detail. More specifically, suture manipulating device 102 has its outer sheath 104 formed out of a tube which is rigid along its entire length, and which has a helical or spiral portion 109 just proximal to its distal end 114. Helical portion 109 is formed so that its distal-most turn 109A will have its longitudinal axis 109B set at an acute angle (e.g. approximately 30 degrees) to the longitudinal axis of the sheath's proximal portion 112, whereby suture can be conveniently coiled about the distal end of sheath 104 when the straight proximal end of sheath 104 is rotated about its longitudinal axis. Helical portion 109 is formed so that the distal end of tool 102 can be passed through the interior passageway of a surgical cannula (shown in phantom as 200 in FIG. 8). Correspondingly, inner rod 106 has at least a portion of its distal end formed out of a flexible material so that inner rod 106 and outer sheath 104 can telescope relative to one another. More specifically, inner rod 106 has a flexible portion 123 set proximal to its distal portion 122 which extends along a sufficiently long portion of inner rod 106 to permit the rod to pass through the outer sheath's helical portion 109. On account of the construction, it will be seen that the inner rod's crochet-type hook 132 can be projected completely out of the sheath's distal end 114 so as to grapple a suture length disposed adjacent the distal end of the tool (in a manner analagous to that shown in FIGS. 4 and 4A), or it can be projected partly out of the sheath's distal end 114 so as to slidingly capture a suture length to the distal end of the tool (in a manner analagous to that shown in FIGS. 5 and 5A), or it can be withdrawn into the sheath's distal end so as to fixedly capture a suture length to the distal end of the tool (in a manner analagous to that shown in FIGS. 6 and 6A).

Suture manipulating device 102 is used in a manner generally analagous to the manner in which suture manipulating device 2 is used, except, of course, that the distal tip of suture manipulating device 102 does not articulate back and forth relative to the proximal portion of the device in the manner that the distal tip of suture manipulating device 2 does. However, in this respect, it will be appreciated that such articulation is provided in the case of suture manipulating device 2 so that the tool's distal tip can be set at an acute angle to the longitudinal axis of the tool's proximal end to facilitate coiling the suture about the exterior of the tool, and such articulation is not necessary in the case of suture manipulating device 102 since the distal tip of the device 102 is permanently set at an angle to the longitudinal axis of the tool's proximal end.

Figure 9:
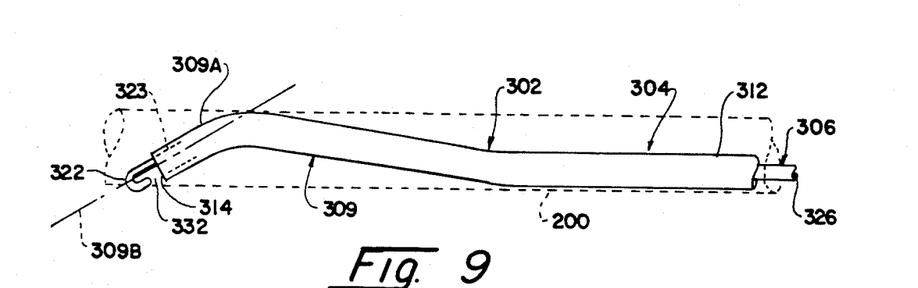
FIG. 9 is a side view in elevation of still another suture manipulating device formed in accordance with the present invention.

Another alternative suture manipulating device is shown in FIG. 9. More specifically, a suture manipulating device 302 is shown which is identical to the suture manipulating device 102, except as will hereinafeter be described in detail. More specifically, suture manipulating device 302 has a bent portion 309 just proximal to its distal end 314. Bent portion 309 is formed so that it has one or more permanent bends disposed in a two-dimensional plane (as opposed to the several permanent bends of tool 102 which are disposed in a three-dimensional sense), and so that its distal-most extension 309A will have its longitudinal axis 309B set at an acute angle (e.g. approximately 30 degrees) to the longitudinal axis of the sheath's proximal portion 312, whereby suture can be conveniently coiled about the distal end of sheath 304 when the straight proximal end 312 of sheath 304 is rotated about its longitudinal axis. Bent portion 309 is formed so that the distal end of tool 302 can be passed through the interior passageway of a surgical cannula (shown in phantom as 200 in FIG. 9). Correspondingly, inner rod 306 has at least a portion of its distal end formed out of a flexible material so that inner rod 306 and outer sheath 304 can telescope relative to one another. More specifically, inner rod 306 has a flexible portion 323 set proximal to its distal portion 322 and set distal to its proximal portion 326. Flexible portion 323 extends along a sufficiently long portion of rod 306 to permit the rod to pass through the outer sheath's bent portion 309. On account of this construction, it will be seen that the inner rod's crochet-type hook 332 can be projected completely out of the sheath's distal end 314 so as to grapple a suture length disposed adjacent the distal end of the tool (in a manner analagous to that shown in FIGS. 4 and 4A), or it can be projected partly out of the sheath's distal end 314 so as to slidingly capture a suture length to the distal end of the tool (in a manner analagous to that shown in FIGS. 5 and 5A), or it can be withdrawn into the sheath's distal end so as to fixedly capture a suture length to the distal end of the tool (in a manner analagous to that shown in FIGS. 6 and 6A).

Suture manipulating device 302 is used in the same manner as suture manipulating device 102.

These and other changes of their type are considered to be within the scope of the present invention.

What is claimed is:

1. A suture manipulating device comprising an outer sheath and an inner rod, said outer sheath comprising a straight, rigid distal portion having a first distal tip, a flexible intermediate portion, and a straight, rigid proximal portion, said flexible intermediate portion of said sheath being formed so that the longitudinal axis of said distal portion of said sheath is normally aligned with the longitudinal axis of said proximal portion of said sheath, and said flexible intermediate portion of said sheath being capable of being elastically deformed so that the longitudinal axis of said distal portion of said sheath can be moved out of alignment with the longitudinal axis of said proximal portion of said sheath;

said inner rod comprising a straight, rigid distal portion having a second distal tip, a bending intermediate portion and a straight, rigid proximal portion, said bending intermediate portion being formed so that the longitudinal axis of said distal portion of said inner rod normally resides at an acute angle relative to the longitudinal axis of said proximal portion of said rod, and said bending intermediate portion being formed so that it is capable of being elastically deformed so that the longitudinal axis of said distal portion of said rod can be brought into alignment with the longitudinal axis of said proximal portion of said rod;

said inner rod further comprising a crochet-type hook disposed adjacent said second distal tip of said inner rod;

said outer sheath and said inner rod being formed so that the length of said distal portion of said outer sheath is approximately the same as the length of said distal portion of said inner rod, and the length of said flexible intermediate portion of said outer sheath is approximately the same as the length of said bending intermediate portion of said inner rod, and said outer sheath and said inner rod also being formed so that said inner rod can make a close sliding fit within the interior of said outer sheath;

said inner rod being positioned within said outer sheath, and said outer sheath and said inner rod being movable relative to one another so as to be able to assume:

(1) a first position where said second distal tip of said inner rod is withdrawn slightly relative to said first distal tip of said outer sheath, and said bending intermediate portion of said inner rod is positioned within and constrained by the straight proximal portion of said outer sheath, whereby said inner rod and said outer sheath will both be substantially straight and in longitudinal alignment with one another;

(2) a second position wherein said distal portion of said inner rod and said bending intermediate portion of said inner rod both project out of said distal portion of said outer sheath, and so that the longitudinal axis of said distal portion of said inner rod is disposed at an acute angle to both the longitudinal axis of said proximal portion of said inner rod and to the longitudinal axis of said outer sheath; and (3) a third position wherein said second distal tip of said inner rod is nearly aligned with said first distal tip of said outer sheath and so that said bending intermediate portion of said inner rod is generally aligned with said flexible intermediate portion of said outer sheath, so that the longitudinal axis of said distal portion of said inner rod will be aligned with the longitudinal axis of said distal portion of said outer sheath, the longitudinal axis of said proximal portion of said inner rod will be aligned with the longitudinal axis of the proximal portion of said outer sheath, and the longitudinal axis of said distal portion of said inner rod will be disposed at an acute angle to the longitudinal axis of said proximal portion of said inner rod.

2. A suture manipulating device according to claim 1 wherein said proximal portion of said outer sheath includes a first proximal end portion, said proximal portion of said inner rod includes a second proximal end portion and said device further comprises operating means attached to said first and second proximal end portions for moving said sheath longitudinally relative to said inner rod.

3. A suture manipulating device according to claim 2 wherein said operating means comprises a handle having a distal handle portion connected to said first proximal end portion of said sheath and a proximal handle portion connected to said second proximal end portion of said inner rod, and further wherein said distal handle portion moves telescopically relative to said proximal handle portion so as to move said sheath longitudinally relative to said inner rod.

4. A suture manipulating device according to claim 1 wherein said distal portion of said sheath is formed out of a material which is at least as soft as the material which is used to form the suture which is to be manipulated by said device.

5. A suture manipulating device according to claim 1 wherein said first distal tip of said sheath is bevelled adjacent its interior bore.

6. A suture manipulating device comprising:
an elongated hollow member comprising a helically-extending distal portion and a longitudinally-extending proximal portion, said helically-extending distal portion terminating in a substantially longitudinally-extending length disposed at an acute angle to said longitudinally-extending proximal portion, said helically-extending distal portion terminating in a distal end surface;
a rod comprising a longitudinally-extending distal portion, a flexible intermediate portion, and a longitudinally-extending proximal portion, said distal portion of said rod terminating in a J-shaped hook, wherein said hook defines a mouth and an interior base and is sized to grapple a suture which is to be manipulated by said device;
said rod being received within the interior of said hollow member and capable of reciprocating relative to said hollow member so that said J-shaped hook can be moved between:
(i) an extended position wherein the mouth of said hook is spaced from said distal end surface of said hollow member by more than the thickness of said suture, whereby said suture can be grappled by said hook;
(ii) an intermediate position wherein the mouth of said hook is spaced from said distal end surface of said hollow member by less than the thickness of said suture, but the interior base of said hook is spaced from said distal end surface of said hollow member by more than the thickness of said suture, whereby a suture grappled by said hook will be slidably captured to said hollow member; and
(iii) a withdrawn position wherein the interior base of said hook is spaced from said distal end surface of said hollow member by less than the thickness of said suture, whereby a suture grappled by said hook will be fixedly captured to said hollow member.

7. A suture manipulating device comprising:
an elongated hollow member comprising a rigid longitudinally-extending distal portion and a rigid longitudinally-extending proximal portion, said longitudinally-extending distal portion being disposed at an acute angle to said longitudinally-extending proximal portion, and said longitudinally-extending distal portion terminating in a distal end surface;
a rod comprising a longitudinally-extending distal portion, a flexible intermediate portion, and a longitudinally-extending proximal portion, said distal portion of said rod terminating in a J-shaped hook, wherein said hook defines a mouth and an interior base and is sized to grapple a suture which is to be manipulated by said device;
said rod being received within the interior of said hollow member and capable of reciprocating relative to said hollow member so that said J-shaped hook can be moved between:
(i) an extended position wherein the mouth of said hook is spaced from said distal end surface of said hollow member by more than the thickness of said suture, whereby said suture can be grappled by said hook;
(ii) an intermediate position wherein the mouth of said hook is spaced from said distal end surface of said hollow member by less than the thickness of said suture, but the interior base of said hook is spaced from said distal end surface of said hollow member by more than the thickness of said suture, whereby a suture grappled by said hook will be slidably captured to said hollow member; and
(iii) a withdrawn position wherein the interior base of said hook is spaced from said distal end surface of said hollow member by less than the thickness of said suture, whereby a suture grappled by said hook will be fixedly captured to said hollow member.

8. A suture manipulating device comprising:
an elongated hollow member comprising a rigid longitudinally-extending distal portion and a rigid longitudinally-extending proximal portion, said longitudinally-extending distal portion being attached to said longitudinally-extending proximal portion so that said longitudinally-extending distal portion can be moved between a first orientation in which said longitudinally-extending distal portion is aligned with said longitudinally-extending proximal portion and a second orientation in which said longitudinally-extending distal portion extends at an acute angle to said longitudinally-extending proximal portion, said longitudinally-extending distal portion terminating in a distal end surface;
a rod comprising a rigid longitudinally-extending distal portion, a flexible intermediate portion, and a rigid longitudinally-extending proximal portion, said distal portion of said rod terminating in a J-shaped hook, wherein said hook defines a mouth and an interior and base a to grapple a suture which is to be manipulated by said device;
said rod being received within the interior of said hollow member and capable of reciprocating relative to said hollow member so that said J-shaped hook can be moved between:
(i) an extended position wherein the mouth of said hook is spaced from said distal end surface of said hollow member by more than the thickness of said suture, whereby said suture can be grappled by said hook;
(ii) an intermediate position wherein the mouth of said hook is spaced from said distal end surface of said hollow member by less than the thickness of said suture, but the interior base of said hook is spaced from said distal end surface of said hollow member by more than the thickness of said suture, whereby a suture grappled by said hook will be slidably captured to said hollow member; and
(iii) a withdrawn position wherein the interior base of said hook is spaced from said distal end surface of said hollow member by less than the thickness of said suture, whereby a suture grappled by said hook will be fixedly captured to said hollow member.

9. A device for manipulating a suture end comprising: a shaft, a flexible rod and hook means;
said shaft including a rigid proximal portion, a rigid distal portion and a distal end;
said distal portion being operatively locatable at an acute angle to said proximal portion;
said rod extending through said shaft and being reciprocally movable therein; and
said hook means being attached to said rod and reciprocally movable relative to said distal end between (1) an open position wherein said hook means is spaced from said distal end by a distance adequate to allow the suture end to be grappled by said hook means; (2) a partially retracted position wherein said hook means and said distal end together define an aperture having a transverse cross-section larger than the transverse cross-section of said suture end; and (3) a fully closed position wherein said hook means and said distal end together define an aperture having a transverse cross-section smaller than the transverse cross-section of said suture end.

10. A method for tying two suture ends together at an interior surgical site, wherein each of said suture ends emanates from a piece of host tissue, said method comprising the steps of:
 (1) providing:
  (a) a suture manipulating device having a distal end and comprising an outer sheath and an inner rod,
   said outer sheath comprising a straight, rigid distal portion having a first distal tip, a flexible intermediate portion, and a straight, rigid proximal portion, said flexible intermediate portion of said sheath being formed so that the longitudinal axis of said distal portion of said sheath is normally aligned with the longitudinal axis of said proximal portion of said sheath, and said flexible intermediate portion of said sheath being capable of being elastically deformed so that the longitudinal axis of said distal portion of said sheath can be moved out of alignment with the longitudinal axis of said proximal portion of said sheath;
   said inner rod comprising a straight, rigid distal portion having a second distal tip, a bending intermediate portion and a straight, rigid proximal portion, said bending intermediate portion being formed so that the longitudinal axis of said distal portion of said inner rod normally resides at an acute angle relative to the longitudinal axis of said proximal portion of said rod, and said bending intermediate portion being formed so that it is capable of being elastically deformed so that the longitudinal axis of said distal portion of said rod can be brought into alignment with the longitudinal axis of said proximal portion of said rod;
   said inner rod further comprising a crochet-type hook disposed adjacent said second distal tip of said inner rod;
   said outer sheath and said inner rod being formed so that the length of said distal portion of said outer sheath is approximately the same as the length of said distal portion of said inner rod, and the length of said flexible intermediate portion of said outer sheath is approximately the same as the length of said bending intermediate portion of said inner rod, and said outer sheath and said inner rod also being formed so that said inner rod can make a close sliding fit within the interior of said outer sheath;
   said inner rod being positioned within said outer sheath, and said outer sheath and said inner rod being movable relative to one another so as to be able to assume:
   (i) a first position wherein said second distal tip of said inner rod is withdrawn slightly relative to said first distal tip of said outer sheath, and said bending intermediate portion of said inner rod is positioned within and constrained by the straight proximal portion of said outer sheath, whereby said inner rod and said outer sheath will both be substantially straight and in longitudinal alignment with one another;
   (ii) a second position wherein said distal portion of said inner rod and said bending intermediate portion of said inner rod both project out of said distal portion of said outer sheath, and so that the longitudinal axis of said distal portion of said inner rod is disposed at an acute angle to both the longitudinal axis of said proximal portion of said inner rod and to the longitudinal axis of said outer sheath; and
   (iii) a third position wherein said second distal tip of said inner rod is nearly aligned with said first distal tip of said outer sheath and so that said bending intermediate portion of said inner rod is generally aligned with said flexible intermediate portion of said outer sheath, so that the longitudinal axis of said distal portion of said inner rod will be aligned with the longitudinal axis of said distal portion of said outer sheath, the longitudinal axis of said proximal portion of said inner rod will be aligned with the longitudinal axis of the proximal portion of said outer sheath, and the longitudinal axis of said distal portion of said inner rod will be disposed at an acute angle to the longitudinal axis of said proximal portion of said inner rod; and
  (b) additional surface holding means having a distal end;
 (2) arranging said suture manipulating device so that it is positioned in its aforementioned first position, and so that its said outer sheath and inner rod are both substantially straight and in longitudinal alignment with one another;
 (3) passing the distal end of said suture manipulating device down a cannula to the interior surgical site so that the distal end of the device is positioned adjacent said suture ends, and passing the distal end of said additional suture holding means down a cannula to the interior surgical site so that the distal end of said additional suture holding means is positioned adjacent said suture ends;
 (4) engaging a first one of said suture ends with said additional suture holding means so as to capture said first one of said suture ends to said additional suture holding means;
 (5) positioning said suture manipulating device in its aforementioned third position so that said distal portions of said outer sheath and said inner rod are set at an acute angle to said proximal portions of said outer sheath and said inner rod;
 (6) winding the length of said first one of said suture ends extending between the host tissue and said additional suture holding means around the distal end of said suture manipulating device so as to form at least one suture coil about said suture manipulating device;
 (7) moving said suture manipulating device out of its aforementioned third position and toward its aforementioned second position so that is crochet-type hook is exposed, engaging a second one of said suture ends in said crochet-type hook and positioning said suture manipulating device in its third position so that said second one of said suture ends is captured between said crochet-type hook of said inner rod and said outer sheath of said suture manipulating device;

(8) pulling said suture manipulating device away from said additional suture holding means so as to draw said second one of said suture ends through said at least one coil of said first one of said suture ends, and so as to thereby form a suture throw; and (9) thereafter repeating the foregoing Steps 4–8 one or more additional times so as to form the desired suture knot.

11. A method according to claim 10 wherein said proximal portion of said outer sheath includes a first proximal end portion, said proximal portion of said inner rod includes a second proximal end portion and said suture manipulating device further comprises operating means attached to said first and second proximal end portions for moving said sheath longitudinally relative to said inner rod.

12. A method according to claim 11 wherein said suture manipulating device further comprises operating means comprising a handle having a distal handle portion connected to said first proximal end portion of said sheath and a proximal handle portion connected to said second proximal end portion of said inner rod, and further wherein said distal handle portion moves telescopically relative to said proximal handle portion so as to move said sheath longitudinally relative to said inner rod.

13. A method according to claim 10 wherein said distal portion of said sheath is formed out of a material which is at least as soft as the material which is used to form said suture.

14. A method according to claim 10 wherein said first distal tip of said sheath is bevelled adjacent its interior bore.

15. A method of tying together two free suture ends emanating from substantially fixed locations comprising:

(a) providing a device for manipulating a suture end comprising:

a shaft, a rod and hook means;

said shaft including a rigid proximal portion, a rigid distal portion and a distal end;

said distal portion being operatively locatable at an acute angle to said proximal portion;

said rod extending through said shaft and being reciprocally movable therein; and said hook means being attached to said rod and reciprocally movable relative to said distal end between (1) an open position wherein said hook means is spaced from said distal end by a distance adequate to allow said suture end to be grappled by said hook means; (2) a partially retracted position wherein said hook means and said distal end together define an aperture having a transverse cross-section larger than the transverse cross-section of said suture end; and (3) a fully closed position wherein said hook means and said distal end together define an aperture having a transverse cross-section smaller than the transverse cross-section of said suture end;

b) restraining a first one of said free suture ends;

c) winding a portion of the length of said first one of said free suture ends around said distal portion of said shaft of said manipulating device so as to form at least one suture coil thereabout;

d) grappling the second of said free suture ends with said hook means of said manipulating device in its open position, and thereafter fixedly capturing said second of said free suture ends against said distal end of said shaft by moving said hook means to its fully closed position; and e) axially withdrawing said manipulating device from said at least one coil so as to draw said second of said free suture ends therethrough.

16. A method according to claim 15 wherein steps (c) to (e) are repeated one or more times.

* * * * *

UNITED STATES PATENT AND TRADEMARK OFFICE
CERTIFICATE OF CORRECTION

PATENT NO. : 5,250,054
DATED : 10/5/93
INVENTOR(S) : Lehmann K. Li

It is certified that error appears in the above-indentified patent and that said Letters Patent is hereby corrected as shown below:

Claim 1, column 14, line 24, delete "where" and insert -- wherein --;

Claim 8, column 16, line 44, delete the phrase "and base a" and insert -- base and is sized --; and Claim 10, column 18, line 37, delete "surface" and insert -- suture --.

Signed and Sealed this

Twenty-second Day of March, 1994

Attest:

BRUCE LEHMAN

Attesting Officer

Commissioner of Patents and Trademarks